United States Patent [19]

Zimmermann

[11] Patent Number: 4,767,859
[45] Date of Patent: Aug. 30, 1988

[54] PROCESS FOR THE PREPARATION OF PTERIDINE DERIVATIVES

[75] Inventor: Pierre Zimmermann, Chaponnay, France

[73] Assignee: Rhone-Poulenc Sante, Courbevoie, France

[21] Appl. No.: 931,053

[22] Filed: Nov. 17, 1986

[30] Foreign Application Priority Data

Nov. 19, 1985 [FR] France .................. 85 17057

[51] Int. Cl.$^4$ .................. A61K 31/495; C07D 475/04; C07D 475/08
[52] U.S. Cl. .................. 544/258; 544/260; 556/410; 556/412
[58] Field of Search ............... 544/258, 260; 556/410, 556/412; 514/249, 258

[56] References Cited

FOREIGN PATENT DOCUMENTS

2135249 12/1972 France .
2163672 7/1973 France .
2351103 12/1977 France .

*Primary Examiner*—Donald G. Daus
*Assistant Examiner*—Mark W. Noel
*Attorney, Agent, or Firm*—Stevens, Davis, Miller & Mosher

[57] ABSTRACT

Pteridine derivatives of general formula

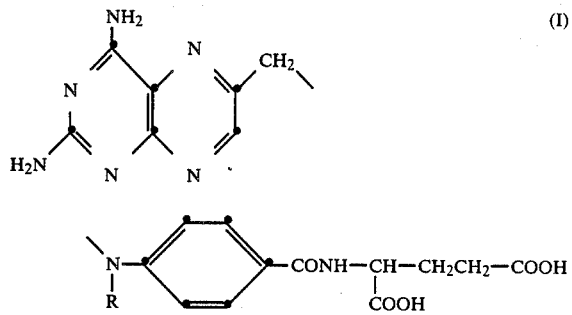

in which R is hydrogen or methyl, i.e. aminopterin or methotrexate, are made by the action of a silazane on a pteridine derivative of formula

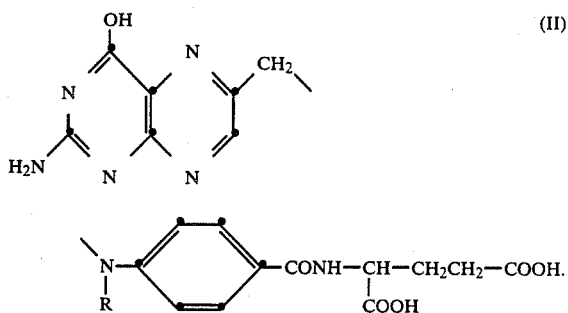

10 Claims, No Drawings

PROCESS FOR THE PREPARATION OF PTERIDINE DERIVATIVES

This Invention provides a process for the preparation of a pteridine of the formula:

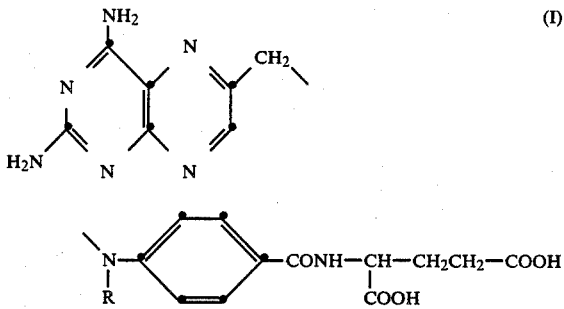

in which R represents hydrogen or methyl, by the amination of a pteridine of formula:

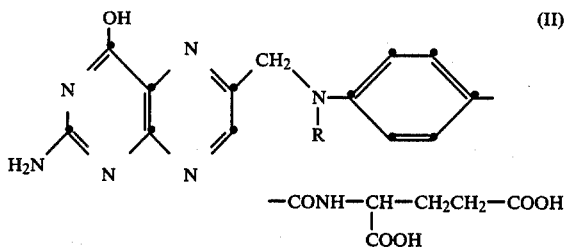

in which R is as defined above.

The product of formula (I) in which R represents a hydrogen atom is aminopterin (N-[4-{N-[(2,4-diamino-6-pteridinyl)methyl]amino}benzoyl]-L-(+)-glutamic acid).

The product of general formula (I) in which R represents a methyl radical is methotrexate (N-[4-{N-[(2,4-diamino-6-pteridinyl)methyl]N-methylamino}benzoyl]-L](+)-glutamic acid) which is an antimitotic used as a folic acid antagonist in the treatment of leukemias.

The product of formula (II) in which R represents a hydrogen atom is folic acid.

The product of formula (II) in which R represents methyl is methopterin (N-[4-{N-[(2-amino-4-hydroxy-6-pteridinyl)methyl]N-methylamino}benzoyl]-L-(+)-glutamic acid).

According to the process described by D. R. Seeger et coll., J. Ameri. Chem. Soc., 71, 1753 (1949), methotrexate is prepared by reacting, in a single operation, 2,4,5,6-tetraminopyrimidine sulfate, sodium N-methyl-p-aminobenzoylglutamate and dibromopropionaldehyde. However, there is no known process for the conversion of folic acid into methotrexate.

Although it is known to prepare methopterin by the methylation of folic acid with formaldehyde in the presence of sodium cyanoborohydride at a pH of about 6.4 according to the process described by CAROLL TEMPLE JR and J. A. MONTGOMERY, J. Med. Chem., 25, 161 (1982), the amination of methopterin has not been described.

It is also known (from French Patent Nos. 2163672 and 2351103) to prepare amino derivatives of nitrogen-containing heterocyclic compounds by the silylation of a heterocyclic compound substituted by one or more hydroxy radicals followed by the action of ammonia or of a primary or secondary amine in the presence of a Lewis acid or of p-toluenesulfonic acid. Hexamethyldisilazane, optionally in the presence of trimethylchlorosilane, hexamethylcyclotrisilazane or octamethylcyclotetrasilazane may be used as silylating agent. When ammonia is used as the aminating agent, it is necessary to operate under a pressure of between 30 and 50 atmospheres, the reaction temperature reaching 180° C.

It is also known from U.S. Pat. No. 3,884,957 to prepare nitriles by heating carboxylic acids with a cyclic or straight-chain silazane in the presence of a Lewis acid such as aluminum chloride or zinc chloride.

It has now been found in a surprising and unexpected way, and this forms the subject of the present invention, that folic acid and methopterin can be aminated by treatment with a silazane so as to replace a hydroxy radical by an amino radical without affecting the rest of the molecule. The process gives aminopterin or methotrexate respectively, in good yield, without the need to use ammonia or to operate under high pressure.

The process of the invention is generally carried out by heating folic acid or methopterin with a silazane such as hexamethyldisilazane.

The reaction is carried out in a basic organic solvent or, if an acidic catalyst is present, in a basic solvent or in acetonitrile.

A tertiary amine such as pyridine, N,N-dimethylaniline or quinoline is generally used as the basic organic solvent. It is particularly advantageous to use pyridine.

When the process is carried out in the presence of a catalyst which is acid in nature, it is particularly advantageous to use as the catalyst an inorganic or organic acid such as hydrochloric, sulfuric, formic or p-toluenesulfonic acid, or a salt which is acid in nature, obtained from an acid and a weaker base, such as an organic or inorganic ammonium salt, e.g. ammonium chloride, sulfate or formate, pyridinium hydrochloride, pyridinium p-toluenesulfonate or N-methyl-anilinium trifluoroacetate. It is also possible to use a Lewis acid such as zinc chloride as the acid catalyst.

When such a catalyst is present, the reaction is advantageously effected in the presence of a basic organic solvent such as pyridine or of acetonitrile.

Pyridinium p-toluenesulfonate in acetonitrile is of very particular value.

The silazane is generally used at a rate of 2 to 10 moles per mole of folic acid or methopterin employed.

When the process is carried out in the presence of p-toluenesulfonic acid, 0.01 to 0.2 mole of catalyst per mole of folic acid or of methopterin employed is generally used.

The reaction temperature is generally between 60° and 180° C. and the reaction is complete after heating for 15 to 25 hours at this temperature.

Aminopterin or methotrexate may be separated from the reaction mixture by the usual extraction technique and may advantageously be isolated in the form of a metal salt such as the sodium salt.

The methotrexate which may contain some unconverted methopterin may be purified by treatment, under the conditions of the amination reaction, with hexamethyldisilazane in the presence of pyridinium p-toluenesulfonate in a suitable organic solvent such as acetonitrile or pyridine.

This process may be applied to the purification of methotrexate originating from any manufacturing process leading to methotrexate contaminated with methopterin.

When the process is carried out starting with folic acid, the aminopterin obtained may be converted into methotrexate by operating under the conditions described by CAROLL TEMPLE JR and J. A. MONTGOMERY, J. Med. Chem., 25, 161 (1982) for the preparation of methopterin from folic acid.

The following examples illustrate the invention.

EXAMPLE 1

Methopterin hydrate (360 mg; 0.75 mmol), anhydrous pyridine (3.6 cc), p-toluenesulfonic acid monohydrate (21 mg; 0.11 mmol) and hexamethyldisilazane (1 cc; 4.74 mmol) are introduced into a 10-cc Hastelloy autoclave. The contents are heated at 100° C. for 21.5 hours, with stirring. After cooling to 20° C., the pyridine solution is concentrated to dryness. The residue obtained is taken up with water (10 cc) and acidified to pH 3.3 by adding normal hydrochloric acid. The yellow precipitate formed is separated by filtration, rinsed with water and washed with ethanol (3 cc). After drying under reduced pressure (0.2 torr) for 15 hours at 20° C., crude methotrexate (340 mg) is obtained.

Analysis by high performance liquid chromatography shows that the degree of conversion is 100% and that the yield is 51.4%.

The product obtained previously (230 mg) is taken up with distilled water (5 cc). The pH is adjusted to 9 by adding normal sodium hydroxide. A small amount of insoluble material is separated by filtration. Acetone (32 cc) is added to the filtrate, with stirring. A yellow precipitate is produced which is separated by filtration and rinsed with acetone. After drying under reduced pressure (0.5 torr) for 24 hours at 20° C., a yellow solid (140 mg) is obtained, which is found by high performance liquid chromatography to contain 81.8% of the sodium salt of methotrexate. The purification yield is 88%.

the structure of the product obtained is confirmed by the infrared spectrum, ultraviolet spectrum and proton nuclear magnetic resonance spectrum.

EXAMPLE 2

Methopterin hydrate (360 mg; 0.75 mmol), anhydrous pyridine (3.6 cc) and hexamethyldisilazane (1 cc; 4.75 mmol) are introduced into a 10-cc autoclave. The contents are stirred at 100° C. for 21 hours 30 minutes.

After cooling to a temperature of about 20° C., the reaction mixture is concentrated to dryness. The residue obtained is taken up with water (10 cc) and then acidified to pH 3.3 by adding N hydrochloric acid. The yellow precipitate formed is separated by filtration, rinsed with water and then washed with ethanol (3 cc). After drying at 20° C. under reduced pressure (1 mm Hg; 0.13 kPa), methotrexate (300 mg) is obtained.

Analysis by high performance liquid chromatography shows that the degree of conversion of methopterin is 88% and that the reaction yield is 48%.

EXAMPLE 3

Folic acid dihydrate (240 mg; 0.50 mmol), anhydrous pyridine (5.48 cc), hexamethyldisilazane (0.65 cc; 3.10 mmol) and p-toluenesulfonic acid monohydrate (17 mg; 0.083 mmol) are introduced into a 10-cc autoclave. The contents are stirred for 17 hours at 100° C. After cooling to 20° C., the reaction mixture is concentrated to dryness. The residue obtained is taken up with water (10 cc) and then made alkaline to pH=9 by adding N sodium hydroxide. A small amount of insoluble material is separated by filtration. After adding acetone (80 cc), a yellow solid precipitates, which is separated by filtration and washed with acetone (5 cc). After drying at 20° C. under reduced pressure (3 mm Hg; 0.4 kPa) for 15 hours, the sodium salt of aminopterin (240 mg; 79% pure) is obtained. The degree of conversion of folic acid is 99.4% and the yield is 78.3%.

The structure of the product obtained is confirmed by the mass spectrum and the nuclear magnetic resonance spectrum.

EXAMPLE 4

Folic acid dihydrate (360 mg; 0.75 mmol), anhydrous pyridine (3.6 cc) and hexamethyldisilazane (1 cc; 4.74 mmol) are introduced into a 10-cc autoclave. The contents are stirred for 48 hours at 100° C. After cooling to 20° C., the reaction mixture is concentrated to dryness. The residue obtained is taken up with water (10 cc) and then made alkaline to pH =9 by adding N sodium hydroxide. Calcium chloride dihydrate (170 mg) and acetone (60 cc) are then added.

The precipitate formed is separated by filtration, washed with acetone (5 cc) and then dried under reduced pressure (3 mm Hg; 0.4 kPa) for 15 hours at 20° C. The calcium salt of aminopterin (440 mg; 33.3% pure) is thereby obtained. The degree of conversion of folic acid is 61.3% and the yield is 41.3%.

EXAMPLE 5

The calcium salt of aminopterin (400 mg; 0.84 mmol) is suspended in distilled water (20 cc). The pH is adjusted to 6.4 by adding N hydrochloric acid. A 37% solution of formaldehyde in water (0.34 cc; 4.20 mmol) and sodium cyanoborohydride (80 mg; 1.27 mmol) are added. The pH is maintained at 6.5 for 4 hours at 20° C. by adding N hydrochloric acid. After 22 hours at 20° C., the pH is adjusted to 9 by adding N sodium hydroxide. Insoluble material is separated by filtration. Calcium chloride dihydrate (190 mg; 1.26 mmol) followed by acetone (100 cc) are added to the filtrate. The precipitate formed is separated by filtration, rinsed with acetone (5 cc) and then dried at 20° C. for 15 hours under reduced pressure (3 mm Hg; 0.4 kPa).

The calcium salt of methotrexate (460 mg; 34.8% pure) is thereby obtained.

EXAMPLE 6

Acetonitrile (90 cc), 96.8% pure methopterin (9 g), para-toluenesulfonic acid monohydrate (0.77 g), pyridine (0.32 cc) and hexamethyldisilazane (26.4 cc) are introduced in sequence into a 250-cc autoclave. The closed autoclave is heated at 100° C. for 18 hours. The pressure is 2 bars. After cooling to a temperature of about 20° C., the reaction mixture is concentrated to a third of its volume (approximately 40 cc). Distilled water (78 cc) is added. A yellow precipitate is formed. A part of the solvent (60 cc) is eliminated by azeotropic distillation under reduced pressure (60 mm Hg; 8kPa). The pH is 4.8. Distilled water (130 cc) is added and the pH is then adjusted to 4 by adding a few drops of N hydrochloric acid. The yellow suspension is stirred for 1 hour at 20° C. The precipitate is separated by filtration and washed with distilled water (2×100 cc).

The precipitate is taken up with distilled water (90 cc) and the pH is adjusted to 9 by adding N sodium hydroxide (33 cc). Acetone (384 cc) is added to the solution obtained. A small amount of precipitate is formed, which is separated by filtration. Acetone (576 cc) is added to the filtrate. The sodium salt of methotrexate precipitates. After 1 hour at a temperature of about 20° C., the precipitate is separated by filtration. The precipitate is washed with acetone (3×15 cc).

The precipitate is dried for 15 hours at 20° C. under reduced pressure (0.1 mm Hg; 0.013 kPa).

The disodium salt of methotrexate (8.10 g) is obtained, having the following characteristics:

Purity (high performance liquid chromatography): 89.1%

Water content: 7.8%

The degree of conversion of methopterin is 99.8% and the yield of 75.7%.

The sodium salt of methotrexate (8.10 g) is dissolved in distilled water (47 cc). The solution is heated to 75° C. and ethanol (249 cc) is then added slowly until a persistent turbidity is obtained. After filtering hot, the filtrate is allowed to cool to a temperature of about 20° C. in the course of approximately 1 hour and is then cooled in a melting icebath for 2 hours 30 minutes. The yellow precipitate is separated by filtration.

The precipitate is dissolved in distilled water (60 cc) and then acidified to pH 4 by adding N hydrochloric acid. The precipitate is separated by filtration and then rinsed with distilled water (20 cc). After drying at 20° C., for 32 hours, under reduced pressure (0.1 mm Hg; 0.013 kPa), 95% pure methotrexate in the acid form (6.57 g), with a water content of 8.4%, is obtained. The yield is 95%.

EXAMPLE 7

Anhydrous pyridine (3.6 cc), methotrexate in the acid form (360 mg, shown by high performance liquid chromatographic analysis to contain 57.6% methotrexate and 20.2% methopterin by area percentage), para-toluenesulfonic acid (22 mg), and hexamethyldisilazane (1 cc) are introduced in sequence into an autoclave. The contents are heated at 100° C. for 16 hours. After cooling, the contents are evaporated to dryness. The residue is taken up with distilled water (approximately 10 cc) and the pH is adjusted to 9 with sodium hydroxide. Calcium chloride dihydrate (170 mg) is added. The addition of acetone (60 cc) leads to the formation of a precipitate which is separated by filtration, drained and rinsed with acetone. After drying at 20° C. for 15 hours under reduced pressure (3 mm Hg; 0.4 kPa), the calcium salt of methotrexate is obtained (440 mg, shown by high performance liquid chromatographic analysis to contain 78.6% methotrexate and 0.45 methopterin by area percentage).

EXAMPLE 8

Anhydrous acetonitrile (3.6 cc), methotrexate in the hydrochloride form (360 mg, shown by high performance liquid chromatographic analysis to contain 89.7% methotrexate and 2.9% methopterin, by area percentage), para-toluenesulfonic acid (25 mg), pyridine (10 cc) and hexamethyldisilazane (0.74 cc) are introduced in sequence into an autoclave. The contents are heated at 100° C. for 7 hours. After cooling, analysis of the reaction mixture by high performance liquid chromatography shows the presence of 87.2% methotrexate and the absence of methopterin (by area percentage).

I claim:

1. A process for the preparation of a pteridine derivative of formula:

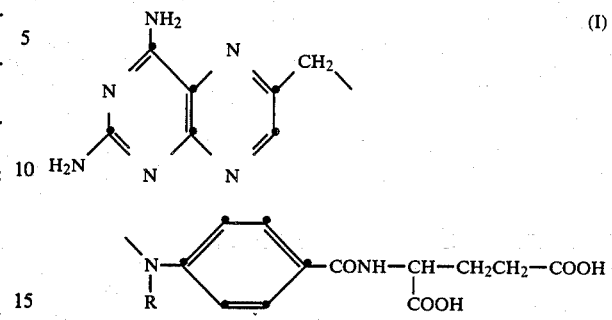

in which R represents hydrogen or methyl, which comprises reacting a pteridine of formula:

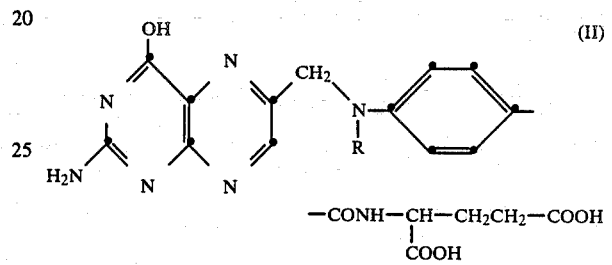

in which R is defined as above, with a silazane in an organic solvent at a temperature from 60 to 180° C., the said solvent being a tertiary amine organic solvent, or, if a catalyst which is acid in nature is present, a basic organic solvent or acetonitrile, and in the absence of ammonia.

2. Process according to claim 1, wherein the silazane used is hexamethyldisilazane.

3. Process according to claim 1, wherein 2 to 10 moles of silazane are used per mol of pteridine derivative of formula II.

4. Process according to claim 1, wherein the basic organic solvent used is pyridine, N,N-dimethylaniline or quinoline.

5. Process according to claim 1, wherein the product of formula 1 is isolated as a metal salt.

6. Process according to claim 1, wherein the reaction is carried out in the presence of a catalyst which is acid in nature in a basic organic solvent or in acetonitrile.

7. Process according to claim 6, wherein the catalyst is an inorganic or organic acid, an organic or inorganic ammonium salt or a Lewis acid.

8. Process according to claim 6, wherein the catalyst is ammonium chloride, sulfate or formate, pyridinium p-toluenesulfonate or hydrochloride or N-methylanilinium trifluoroacetate.

9. Process according to claim 6, wherein the acidic catalyst is pyridinium p-toluenesulfonate and the solvent is acetonitrile.

10. A process for the purification of methotrexate containing methopterin, which comprises subjecting the impure methotrexate to the action of a silazane in pyridine in the presence of pyridinium p-toluenesulfonate at a temperature from 60° to 180° C. and isolating the purified methotrexate.

* * * * *